US010207971B2

(12) United States Patent
Deur-Bert et al.

(10) Patent No.: US 10,207,971 B2
(45) Date of Patent: Feb. 19, 2019

(54) COMPOSITIONS COMPRISING 1,1,1,2,3 PENTACHLOROPROPANE

(71) Applicant: Arkema France, Colombes (FR)

(72) Inventors: Dominique Deur-Bert, Charly (FR); Laurent Wendlinger, Soucieu En Jarrest (FR); Bertrand Collier, Saint-genis-laval (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/518,605

(22) PCT Filed: Oct. 7, 2015

(86) PCT No.: PCT/FR2015/052692
§ 371 (c)(1),
(2) Date: Apr. 12, 2017

(87) PCT Pub. No.: WO2016/059322
PCT Pub. Date: Apr. 21, 2016

(65) Prior Publication Data
US 2017/0226035 A1 Aug. 10, 2017

(30) Foreign Application Priority Data
Oct. 16, 2014 (FR) ..................................... 14 59926

(51) Int. Cl.
C07C 19/01 (2006.01)
C07C 17/20 (2006.01)
C07C 17/25 (2006.01)

(52) U.S. Cl.
CPC ............ C07C 19/01 (2013.01); C07C 17/206 (2013.01); C07C 17/25 (2013.01)

(58) Field of Classification Search
CPC .......... C07C 19/01; C07C 21/18; C07C 19/10
See application file for complete search history.

(56) References Cited

U.S. PATENT DOCUMENTS

| 9,663,425 | B2 * | 5/2017 | Yang | ........................ C07C 17/25 |
| 2012/0157723 | A1 | 6/2012 | Fukuju et al. | |
| 2013/0267740 | A1 * | 10/2013 | Wendlinger | .......... C07C 17/206 570/156 |
| 2014/0031597 | A1 * | 1/2014 | Deur-Bert | ............. C07C 17/206 570/160 |
| 2014/0206911 | A1 | 7/2014 | Sherwood et al. | |
| 2014/0228601 | A1 * | 8/2014 | Dawkins | ................. C07C 17/38 570/230 |

FOREIGN PATENT DOCUMENTS

WO WO-2013/088195 6/2013

OTHER PUBLICATIONS

International Search Report dated Jan. 21, 2016 for PCT/FR2015/052692.

* cited by examiner

Primary Examiner — Jafar F Parsa
(74) Attorney, Agent, or Firm — NK Patent Law

(57) ABSTRACT

The invention relates to a composition comprising at least 99% by weight of 1,1,1,2,3-pentachloropropane, and comprising at least one compound chosen from a list of additional compounds consisting of trichloropropanes, tetrachloropropanes, pentachloropropanes other than 1,1,1,2,3-pentachloropropane, hexachloropropanes, heptachloropropanes, dichloropropenes, trichloropropenes, tetrachloropropenes, pentachloropropenes and hexachloropropene, said compound being present in the composition in a weight content of less than or equal to 500 ppm.
The invention also relates to the use of this composition for manufacturing 2,3,3,3-tetrafluoropropene.

11 Claims, No Drawings

COMPOSITIONS COMPRISING 1,1,1,2,3 PENTACHLOROPROPANE

CROSS-REFERENCE TO RELATED APPLICATIONS

This application is a U.S. National Stage application of International Application No. PCT/FR2015/052692, filed Oct. 7, 2015, which claims the benefit of French Application No. 1459926, filed Oct. 16, 2014.

FIELD OF THE INVENTION

The present invention relates to compositions based on F-240db (1,1,1,2,3-pentachloropropane) and also to the use thereof especially for producing F-1234yf (2,3,3,3-tetrafluoropropene).

TECHNICAL BACKGROUND

F-1234yf is a compound of major interest for refrigeration and air conditioning systems, given the new environmental regulations.

It is known practice to produce hydrofluoroolefins such as F-1234yf by fluorination of hydrochloroolefins or chlorohydrocarbons, especially. This fluorination is generally a catalytic fluorination using hydrofluoric acid as fluorinating agent.

Among the routes for obtaining F-1234yf, it is in particular known practice to use F-240db (1,1,1,2,3-pentachloropropane) as starting compound. Reference is made, for example, to WO 2013/088 195 in this respect.

It is desirable to be able to produce F-1234yf with a low content of impurities. In particular, the formation of certain toxic and/or flammable impurities and/or impurities that are difficult to separate from F-1234yf should be minimized.

There is thus a need to provide means for obtaining F-1234yf compositions of satisfactory purity.

SUMMARY OF THE INVENTION

The invention relates firstly to a composition comprising at least 99% by weight of 1,1,1,2,3-pentachloropropane, and comprising at least one compound chosen from a list of additional compounds consisting of trichloropropanes, tetrachloropropanes, pentachloropropanes other than 1,1,1,2,3-pentachloropropane, hexachloropropanes, heptachloropropanes, dichloropropenes, trichloropropenes, tetrachloropropenes, pentachloropropenes and hexachloropropene, said compound being present in the composition in a weight content of less than or equal to 500 ppm.

According to one embodiment, said compound is present in the composition in a weight content of less than or equal to 250 ppm; preferably less than or equal to 150 ppm; more particularly less than or equal to 100 ppm; more particularly less than or equal to 50 ppm; and ideally less than or equal to 10 ppm.

According to one embodiment, the composition comprises a plurality of compounds chosen from said list of additional compounds, each of the compounds of said plurality of compounds being present in the composition in a weight content of less than or equal to 500 ppm; preferably less than or equal to 250 ppm; preferably less than or equal to 150 ppm; more particularly less than or equal to 100 ppm; more particularly less than or equal to 50 ppm; and ideally less than or equal to 10 ppm.

According to one embodiment, the composition comprises a plurality of compounds chosen from said list of additional compounds, the total weight content of all of the compounds of said list being less than or equal to 1000 ppm; preferably less than or equal to 500 ppm; preferably less than or equal to 250 ppm; preferably less than or equal to 150 ppm; more particularly less than or equal to 100 ppm; more particularly less than or equal to 50 ppm; and ideally less than or equal to 10 ppm.

According to one embodiment, the composition comprises at least 99.5% by weight, preferably at least 99.8% by weight, and more particularly preferably at least 99.9% by weight, of 1,1,1,2,3-pentachloropropane.

According to one embodiment, the composition comprises at least one compound chosen from the group consisting of 1,1,1,3-tetrachloropropane, 3,3,3-trichloropropene and 1,1,3-trichloropropene; and the weight content of each of these compounds in the composition is less than or equal to 100 ppm, preferably less than or equal to 50 ppm; and, optionally, the total weight content of the compounds of this group in the composition is less than or equal to 100 ppm, preferably less than or equal to 50 ppm.

According to one embodiment, the composition comprises at least one compound chosen from trichloropropenes and tetrachloropropanes, the weight content of each of these compounds in the composition being less than or equal to 250 ppm, preferably less than or equal to 150 ppm; and, optionally, the total weight content of the trichloropropenes and tetrachloropropanes in the composition is less than or equal to 250 ppm, preferably less than or equal to 150 ppm.

According to one embodiment, the composition comprises at least one compound chosen from pentachloropropenes and hexachloropropanes, the weight content of each of these compounds in the composition being less than or equal to 50 ppm, preferably less than or equal to 10 ppm; and, optionally, the total weight content of the pentachloropropenes and hexachloropropanes in the composition is less than or equal to 50 ppm, preferably less than or equal to 10 ppm.

According to one embodiment, the composition comprises at least one compound chosen from hexachloropropene and heptachloropropanes, the weight content of each of these compounds in the composition being less than or equal to 50 ppm, preferably less than or equal to 10 ppm; and, optionally, the total weight content of hexachloropropene and of heptachloropropanes in the composition is less than or equal to 50 ppm, preferably less than or equal to 10 ppm.

According to one embodiment, the composition comprises at least one compound chosen from dichloropropenes and trichloropropanes, the weight content of each of these compounds in the composition being less than or equal to 50 ppm, preferably less than or equal to 10 ppm; and, optionally, the total weight content of the dichloropropenes and trichloropropanes in the composition is less than or equal to 50 ppm, preferably less than or equal to 10 ppm.

According to one embodiment, the composition comprises at least one compound chosen from the group consisting of 1,1,3,3-tetrachloropropene, 1,3,3,3-tetrachloropropene, 1,1,1,3,3-pentachloropropane and 1,1,2,3,3-pentachloropropane, and the weight content of each of these compounds in the composition is less than or equal to 500 ppm, preferably less than or equal to 300 ppm; and, optionally, the total weight content of the compounds of this group in the composition is less than or equal to 500 ppm, preferably less than or equal to 300 ppm.

The invention also relates to a process for producing 2,3,3,3-tetrafluoropropene, comprising:

the provision of a composition as described above;
the reaction of this composition with hydrofluoric acid in the gas phase.

According to one embodiment, the process comprises a single step of catalytic fluorination.

According to one embodiment, the process comprises two successive steps of catalytic fluorination, namely:
the reaction of the composition with hydrofluoric acid in the gas phase, to manufacture an intermediate product;
optionally, purification of the intermediate product; and then
reaction of the intermediate product with hydrofluoric acid in the gas phase, to manufacture 2,3,3,3-tetrafluoropropene;
the intermediate product preferably being 2-chloro-3,3,3-trifluoropropene.

The present invention makes it possible to overcome the drawbacks of the prior art. It more particularly provides compositions based on F-240db, the content of impurities of which makes it possible to minimize the presence of harmful impurities in the F-1234yf manufactured therefrom.

Specifically, the impurities present in F-1234yf are partly dependent on the impurities initially present in the F-240db which is used to manufacture it. In the course of the fluorination reaction(s), some of the impurities of F-240db may be converted into different impurities in F-1234yf. Controlling the impurities present in F-240db thus makes it possible indirectly to control the impurities present in F-1234yf.

Such an indirect control may be advantageous insofar as the impurities of F-1234yf may be more difficult to separate from F-1234yf than the impurities of F-240db relative to F-240db. This is especially the case when the impurities of F-1234yf have a very close boiling point or form an azeotrope or a quasi-azeotrope therewith.

DESCRIPTION OF EMBODIMENTS OF THE INVENTION

The invention is now described in greater detail and in a nonlimiting manner in the description that follows.

All the contents indicated are weight contents, unless otherwise mentioned.

Nomenclature

The table below gives the nomenclature of a certain number of compounds that are included in the invention.

| Formula | Notation | Full name |
|---|---|---|
| $CF_3$—$CH_3$ | F-143a | 1,1,1-trifluoroethane |
| $CCl_3$—CHCl—$CCl_3$ | F-220da | 1,1,1,2,3,3,3-heptachloropropane |
| $CHCl_2$—$CCl_2$—$CCl_3$ | F-220aa | 1,1,1,2,2,3,3-heptachloropropane |
| $CF_3$—CHCl—$CF_3$ | F-226da | 2-chloro-1,1,1,3,3,3-hexafluoropropane |
| $CF_3$—CHF—$CClF_2$ | F-226ea | 1-chloro-1,1,2,3,3,3-hexafluoropropane |
| $CF_3$—CFCl—$CHF_2$ | F-226ba | 2-chloro-1,1,2,3,3,3-hexafluoropropane |
| $CF_3$—$CF_2$—CHFCl | F-226ca | 3-chloro-1,1,1,2,2,3-hexafluoropropane |
| $CClF_2$—$CF_2$—$CHF_2$ | F-226cb | 1-chloro-1,1,2,2,3,3-hexafluoropropane |
| $CCl_3$—$CH_2$—$CCl_3$ | F-230fa | 1,1,1,3,3,3-hexachloropropane |
| $CHCl_2$—CHCl—$CCl_3$ | F-230da | 1,1,1,2,3,3-hexachloropropane |
| $CHCl_2$—$CCl_2$—$CHCl_2$ | F-230aa | 1,1,2,2,3,3-hexachloropropane |
| $CH_2Cl$—$CCl_2$—$CCl_3$ | F-230ab | 1,1,1,2,2,3-hexachloropropane |
| $CF_3$—$CH_2$—$CF_2Cl$ | F-235fa | 3-chloro-1,1,1,3,3-pentafluoropropane |
| $CF_3$—CHF—CHFCl | F-235ea | 1-chloro-1,2,3,3,3-pentafluoropropane |
| $CHF_2$—CHF—$CClF_2$ | F-235eb | 1-chloro-1,1,2,3,3-pentafluoropropane |
| CHClF—$CF_2$—$CHF_2$ | F-235ca | 3-chloro-1,1,2,2,3-pentafluoropropane |
| $CH_2Cl$—$CF_2$—$CF_3$ | F-235cb | 3-chloro-1,1,1,2,2-pentafluoropropane |
| $CH_2F$—$CF_2$—$CClF_2$ | F-235cc | 1-chloro-1,1,2,2,3-pentafluoropropane |
| $CHF_2$—CHCl—$CF_3$ | F-235da | 2-chloro-1,1,1,3,3-pentafluoropropane |
| $CHF_2$—CClF—$CHF_2$ | F-235ba | 2-chloro-1,1,2,3,3-pentafluoropropane |
| $CH_2F$—CClF—$CF_3$ | F-235bb | 2-chloro-1,1,1,2,3-pentafluoropropane |
| $CF_3$—C—$CF_3$ | F-236fa | 1,1,1,3,3,3-hexafluoropropane |
| $CHF_2$—$CF_2$—$CHF_2$ | F-236ca | 1,1,2,2,3,3-hexafluoropropane |
| $CH_2F$—$CF_2$—$CF_3$ | F-236cb | 1,1,1,2,2,3-hexafluoropropane |
| $CHF_2$—CHF—$CF_3$ | F-236ea | 1,1,1,2,3,3-hexafluoropropane |
| $CHCl_2$—$CH_2$—$CCl_3$ | F-240fa | 1,1,1,3,3-pentachloropropane |
| $CHCl_2$—CHCl—$CHCl_2$ | F-240da | 1,1,2,3,3-pentachloropropane |
| $CH_2Cl$—CHCl—$CCl_3$ | F-240db | 1,1,1,2,3-pentachloropropane |
| $CH_2Cl$—$CCl_2$—$CHCl_2$ | F-240aa | 1,1,2,2,3-pentachloropropane |
| $CH_3$—$CCl_2$—$CCl_3$ | F-240ab | 1,1,1,2,2-pentachloropropane |
| $CH_2F$—$CF_2$—$CHF_2$ | F-245ca | 1,1,2,2,3-pentafluoropropane |
| $CF_3$—$CF_2$—$CH_3$ | F-245cb | 1,1,1,2,2-pentafluoropropane |
| $CHF_2$—CHF—$CHF_2$ | F-245ea | 1,1,2,3,3-pentafluoropropane |
| $CH_2F$—CHF—$CF_3$ | F-245eb | 1,1,1,2,3-pentafluoropropane |
| $CHF_2$—$CH_2$—$CF_3$ | F-245fa | 1,1,1,3,3-pentafluoropropane |
| $CHCl_2$—$CH_2$—$CHCl_2$ | F-250fa | 1,1,3,3-tetrachloropropane |
| $CH_2Cl$—$CH_2$—$CCl_3$ | F-250fb | 1,1,1,3-tetrachloropropane |
| $CH_2Cl$—CHCl—$CHCl_2$ | F-250da | 1,1,2,3-tetrachloropropane |
| $CH_3$—CHCl—$CCl_3$ | F-250db | 1,1,1,2-tetrachloropropane |
| $CH_2Cl$—$CCl_2$—$CH_2Cl$ | F-250aa | 1,2,2,3-tetrachloropropane |
| $CH_3$—$CCl_2$—$CHCl_2$ | F-250ab | 1,1,2,2-tetrachloropropane |
| $CF_2Cl$—$CH_2$—$CH_2F$ | F-253fa | 1-chloro-1,1,3-trifluoropropane |
| $CH_2Cl$—$CH_2$—$CF_3$ | F-253fb | 1-chloro-3,3,3-trifluoropropane |
| $CF_2Cl$—$CH_2$—$CH_2F$ | F-253fc | 1-chloro-1,1,3-trifluoropropane |
| $CH_2F$—CClF—$CH_2F$ | F-253ba | 2-chloro-1,2,3-trifluoropropane |
| $CHF_2$—CClF—$CH_3$ | F-253bb | 2-chloro-1,1,2-trifluoropropane |
| $CH_2Cl$—$CF_2$—$CH_2F$ | F-253ca | 1-chloro-2,2,3-trifluoropropane |
| CHFCl—$CF_2$—$CH_3$ | F-253cb | 1-chloro-1,2,2-trifluoropropane |
| $CHF_2$—CHF—$CH_2Cl$ | F-253ea | 3-chloro-1,1,2-trifluoropropane |
| CHClF—CHF—$CH_2F$ | F-253eb | 1-chloro-1,2,3-trifluoropropane |
| $CClF_2$—CHF—$CH_3$ | F-253ec | 1-chloro-1,1,2-trifluoropropane |
| $CH_2Cl$—$CH_2$—$CHCl_2$ | F-260fa | 1,1,3-trichloropropane |
| $CH_3$—$CH_2$—$CCl_3$ | F-260fb | 1,1,1-trichloropropane |
| $CH_2Cl$—CHCl—$CH_2Cl$ | F-260da | 1,2,3-trichloropropane |
| $CH_3$—CHCl—$CHCl_2$ | F-260db | 1,1,2-trichloropropane |
| $CH_3$—$CCl_2$—$CH_2Cl$ | F-260aa | 1,2,2-trichloropropane |
| $CCl_3$—CCl=$CCl_2$ | F-1210xa | hexachloropropene |
| $CF_3$—CCl=$CCl_2$ | F-1213xa | 1,1,2-trichloro-3,3,3-trifluoropropene |
| $CF_2Cl$—CCl=CFCl | F-1213xb | 1,2,3-trichloro-1,3,3-trifluoropropene |
| $CFCl_2$—CCl=$CF_2$ | F-1213xc | 2,3,3-trichloro-1,1,3-trifluoropropene |
| $CCl_3$—CF=$CF_2$ | F-1213yc | 3,3,3-trichloro-1,1,2-trifluoropropene |
| $CFCl_2$—CF=CFCl | F-1213yb | 1,3,3-trichloro-1,2,3-trifluoropropene |
| $CF_2Cl$—CF=$CCl_2$ | F-1213ya | 1,1,3-trichloro-2,3,3-trifluoropropene |
| $CCl_2F$—CF=$CF_2$ | F-1214yc | 3,3-dichloro-1,1,2,3-tetrafluoropropene |
| $CClF_2$—CCl=$CF_2$ | F-1214xc | 2,3-dichloro-1,1,3,3-tetrafluoropropene |
| $CClF_2$—CF=CFCl | F-1214yb | 1,3-dichloro-1,2,3,3-tetrafluoropropene |
| $CF_3$—CCl=CFCl | F-1214xb | 1,2-dichloro-1,3,3,3-tetrafluoropropene |
| $CF_3$—CF=$CCl_2$ | F-1214ya | 1,2-dichloro-2,3,3,3-tetrafluoropropene |
| $CF_3$—CF=$CF_2$ | F-1216yc | hexafluoropropene |
| $CHCl_2$—CCl=$CCl_2$ | F-1220xa | 1,1,2,3,3-pentachloropropene |
| $CCl_3$—CCl=CHCl | F-1220xd | 1,2,3,3,3-pentachloropropene |
| $CCl_3$—CH=$CCl_2$ | F-1220za | 1,1,3,3,3-pentachloropropene |
| $CF_3$—CCl=CHCl | F-1223xd | 1,2-dichloro-3,3,3-trifluoropropene |
| $CF_2Cl$—CCl=CHF | F-1223xe | 2,3-dichloro-1,3,3-trifluoropropene |
| CHFCl—CCl=$CF_2$ | F-1223xc | 2,3-dichloro-1,1,3-trifluoropropene |
| $CFCl_2$—CH=$CF_2$ | F-1223zc | 3,3-dichloro-1,1,3-trifluoropropene |
| $CF_2Cl$—CH=CFCl | F-1223zb | 1,3-dichloro-1,3,3-trifluoropropene |
| $CF_3$—CH=$CCl_2$ | F-1223za | 1,1-dichloro-3,3,3-trifluoropropene |
| $CHF_2$—CF=$CCl_2$ | F-1223ya | 1,1-dichloro-2,3,3-trifluoropropene |
| $CF_2Cl$—CF=CHCl | F-1223yd | 1,3-dichloro-2,3,3-trifluoropropene |
| $CFCl_2$—CF=CHF | F-1223ye | 3,3-dichloro-1,2,3-trifluoropropene |
| $CHCl_2$—CF=$CF_2$ | F-1223yc | 3,3-dichloro-1,1,2-trifluoropropene |
| CHFCl—CF=$CF_2$ | F-1224yc | 3-chloro-1,1,2,3-tetrafluoropropene |
| $CHF_2$—CCl=$CF_2$ | F-1224xc | 2-chloro-1,1,3,3-tetrafluoropropene |
| $CF_2Cl$—CH=$CF_2$ | F-1224zc | 3-chloro-1,1,3,3-tetrafluoropropene |
| $CHF_2$—CF=CFCl | F-1224yb | 1-chloro-1,2,3,3-tetrafluoropropene |
| $CF_3$—CH=CFCl | F-1224zb | 1-chloro-1,3,3,3-tetrafluoropropene |
| $CClF_2$—CF=CHF | F-1224ye | 3-chloro-1,2,3,3-tetrafluoropropene |
| $CF_3$—CCl=CHF | F-1224xe | 2-chloro-1,3,3,3-tetrafluoropropene |
| $CF_3$—CF=CHCl | F-1224yd | 1-chloro-2,3,3,3-tetrafluoropropene |
| $CF_3$—CH=$CF_2$ | F-1225zc | 1,1,3,3,3-pentafluoropropene |
| $CHF_2$—CF=$CF_2$ | F-1225yc | 1,1,2,3,3-pentafluoropropene |
| $CF_3$—CF=CHF | F-1225ye | 1,2,3,3,3-pentafluoropropene |
| $CH_2Cl$—CCl=$CCl_2$ | F-1230xa | 1,1,2,3-tetrachloropropene |
| $CHCl_2$—CCl=CHCl | F-1230xd | 1,2,3,3-tetrachloropropene |
| $CCl_3$—CCl=$CH_2$ | F-1230xf | 2,3,3,3-tetrachloropropene |
| $CHCl_2$—CH=$CCl_2$ | F-1230za | 1,1,3,3-tetrachloropropene |

-continued

| Formula | Notation | Full name |
|---|---|---|
| CCl$_3$—CH=CHCl | F-1230zd | 1,3,3-tetrachloropropene |
| CF$_3$—CCl=CH$_2$ | F-1233xf | 2-chloro-3,3,3-trifluoropropene |
| CClF$_2$—CF=CH$_2$ | F-1233yf | 3-chloro-2,3,3-trifluoropropene |
| CHF$_2$—CF=CHCl | F-1233yd | 1-chloro-2,3,3-trifluoropropene |
| CF$_3$—CH=CHCl | F-1233zd | 1-chloro-3,3,3-trifluoropropene |
| CHF$_2$—CCl=CHF | F-1233xe | 2-chloro-1,3,3-trifluoropropene |
| CHClF—CF=CHF | F-1233ye | 3-chloro-1,2,3-trifluoropropene |
| CClF$_2$—CH=CHF | F-1233ze | 3-chloro-1,3,3-trifluoropropene |
| CH$_2$Cl—CF=CF$_2$ | F-1233yc | 3-chloro-1,1,2-trifluoropropene |
| CFH$_2$—CCl=CF$_2$ | F-1233xc | 2-chloro-1,1,3-trifluoropropene |
| CFClH—CH=CF$_2$ | F-1233zc | 3-chloro-1,1,3-trifluoropropene |
| CFH$_2$—CF=CFCl | F-1233yb | 1-chloro-1,2,3-trifluoropropene |
| CF$_2$H—CH=CFCl | F-1233zb | 1-chloro-1,3,3-trifluoropropene |
| CF$_3$—CF=CH$_2$ | F-1234yf | 2,3,3,3-tetrafluoropropene |
| CF$_3$—CH=CHF | F-1234ze | 1,3,3,3-tetrafluoropropene |
| CH$_2$F—CF=CF$_2$ | F-1234yc | 1,1,2,3-tetrafluoropropene |
| CHF$_2$—CH=CF$_2$ | F-1234zc | 1,1,3,3-tetrafluoropropene |
| CHF$_2$—CF=CHF | F-1234ye | 1,2,3,3-tetrafluoropropene |
| CH$_3$—CCl=CCl$_2$ | F-1240xa | 1,1,2-trichloropropene |
| CH$_2$Cl—CCl=CHCl | F-1240xd | 1,2,3-trichloropropene |
| CHCl$_2$—CCl=CH$_2$ | F-1240xf | 2,3,3-trichloropropene |
| CH$_2$Cl—CH=CCl$_2$ | F-1240za | 1,1,3-trichloropropene |
| CHCl$_2$—CH=CHCl | F-1240zd | 1,3,3-trichloropropene |
| CCl$_3$—CH=CH$_2$ | F-1240zf | 3,3,3-trichloropropene |
| CClF$_2$—CH=CH$_2$ | F-1242zf | 3-chloro-3,3-difluoropropene |
| CHClF—CF=CH$_2$ | F-1242yf | 3-chloro-2,3-difluoropropene |
| CHF$_2$—CCl=CH$_2$ | F-1242xf | 2-chloro-3,3-difluoropropene |
| CH$_3$—CCl=CF$_2$ | F-1242xc | 2-chloro-1,1-difluoropropene |
| CH$_2$Cl—CH=CF$_2$ | F-1242zc | 3-chloro-1,1-difluoropropene |
| CH$_2$Cl—CF=CHF | F-1242ye | 3-chloro-1,2-difluoropropene |
| CH$_2$F—CCl=CHF | F-1242xe | 2-chloro-1,3-difluoropropene |
| CHFCl—CH=CHF | F-1242ze | 3-chloro-1,3-difluoropropene |
| CH$_2$F—CF=CHCl | F-1242yd | 1-chloro-2,3-difluoropropene |
| CHF$_2$—CH=CHCl | F-1242zd | 1-chloro-3,3-difluoropropene |
| CH$_2$F—CH=CF$_2$ | F-1243zc | 1,1,3-trifluoropropene |
| CH$_3$—CF=CF$_2$ | F-1243yc | 1,1,2-trifluoropropene |
| CF$_3$—CH=CH$_2$ | F-1243zf | 3,3,3-trifluoropropene |
| CH$_2$F—CF=CHF | F-1243ye | 1,2,3-trifluoropropene |
| CHF$_2$—CF=CH$_2$ | F-1243yf | 2,3,3-trifluoropropene |
| CHF$_2$—CH=CHF | F-1243ze | 1,3,3-trifluoropropene |
| CH$_3$—CH=CCl$_2$ | F-1250za | 1,1-dichloropropene |
| CH$_3$—CCl=CHCl | F-1250xd | 1,2-dichloropropene |
| CH$_2$Cl—CCl=CH$_2$ | F-1250xf | 2,3-dichloropropene |
| CH$_2$Cl—CH=CHCl | F-1250zd | 1,3-dichloropropene |
| CHCl$_2$—CH=CH$_2$ | F-1250zf | 3,3-dichloropropene |
| CH$_3$—CH=CF$_2$ | F-1252zc | 1,1-difluoropropene |
| CH$_3$—CF=CHF | F-1252ye | 1,2-difluoropropene |
| CH$_2$F—CF=CH$_2$ | F-1252yf | 2,3-difluoropropene |
| CHF$_2$—CH=CH$_2$ | F-1252zf | 3,3-difluoropropene |

When the above compounds exist in the form of two cis and trans isomers, the name of the compound (for example F-1234ze) denotes, without preference, one or the other form or a mixture of the two forms. The maximum contents indicated are then total contents with respect to the two possible forms.

Moreover, the name "F-220" generically denotes all of the heptachloropropane compounds, the name "F-230" generically denotes all of the hexachloropropane compounds, and so on, using the notations of the above table without the final two letters.

Compositions According to the Invention

The invention proposes compositions based on F-240db. The content of F-240db is greater than or equal to 99%.

According to certain embodiments, it is greater than or equal to 99.1%, or to 99.2%, or to 99.3%, or to 99.4%, or to 99.5%, or to 99.6%, or to 99.7%, or to 99.8%, or to 99.9%.

The compositions according to the invention also comprise at least one compound chosen from a list of additional compounds which is constituted by the series F-220, F-230, F-240 (with the exception of F-240db), F-250, F-260 and by the series F-1210, F-1220, F-1230, F-1240 and F-1250, said compound being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

Said at least one compound may be present in a content of greater than or equal to 1 ppm, or greater than or equal to 2 ppm, or greater than or equal to 3 ppm, or greater than or equal to 5 ppm.

For example, said at least one compound may be present in a content of from 1 to 5 ppm; or in a content of from 5 to 10 ppm; or in a content of from 10 to 25 ppm; or in a content of from 25 to 50 ppm; or in a content of from 50 to 75 ppm; or in a content of from 75 to 100 ppm; or in a content of from 100 to 150 ppm; or in a content of from 150 to 200 ppm; or in a content of from 200 to 250 ppm; or in a content of from 250 to 300 ppm; or in a content of from 300 to 350 ppm; or in a content of from 350 to 400 ppm; or in a content of from 400 to 450 ppm; or in a content of from 450 to 500 ppm.

One embodiment relates to such compositions which comprise a plurality (two, three, four or more than four) compounds chosen from the list of additional compounds above, the content of each of said compounds being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

Each compound of this plurality may then be present in a content of greater than or equal to 1 ppm, or greater than or equal to 2 ppm, or greater than or equal to 3 ppm, or greater than or equal to 5 ppm.

For example, each compound of this plurality may be present in a content of from 1 to 5 ppm; or in a content of from 5 to 10 ppm; or in a content of from 10 to 25 ppm; or in a content of from 25 to 50 ppm; or or in a content of from 50 to 75 ppm; or in a content of from 75 to 100 ppm; or in a content of from 100 to 150 ppm; or in a content of from 150 to 200 ppm; or in a content of from 200 to 250 ppm; or in a content of from 250 to 300 ppm; or in a content of from 300 to 350 ppm; or in a content of from 350 to 400 ppm; or in a content of from 400 to 450 ppm; or in a content of from 450 to 500 ppm.

One embodiment relates to such compositions in which the content of each of the compounds of the list of additional compounds above optionally present in the composition (with the exception of F-240aa, F-1230xf and F-1230xa, which may optionally be present in larger amounts) is less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

Each compound of the list of additional compounds may then be present in a content of greater than or equal to 1 ppm, or greater than or equal to 2 ppm, or greater than or equal to 3 ppm, or greater than or equal to 5 ppm.

For example, each compound of the list of additional compounds (with the exception of F-240aa, F-1230xf and F-1230xa, which may optionally be present in larger amounts) may be present in a content of from 1 to 5 ppm; or in a content of from 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

The compositions according to the invention may especially comprise one or more compounds of the series F-220, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-220 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-220 may then be present in a content of greater than or equal to 1 ppm, or greater than or equal to 2 ppm, or greater than or equal to 3 ppm, or greater than or equal to 5 ppm. Similarly, the total content of compounds of the series F-220 in the composition may be greater than or equal to 1 ppm, or greater than or equal to 2 ppm, or greater than or equal to 3 ppm, or greater than or equal to 5 ppm.

For example, the compound(s) of the series F-220 may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-220 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-230, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-230 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-230 may then be present in a content of greater than or equal to 1 ppm, or greater than or equal to 2 ppm, or greater than or equal to 3 ppm, or greater than or equal to 5 ppm. Similarly, the total content of compounds of the series F-230 in the composition may be greater than or equal to 1 ppm, or greater than or equal to 2 ppm, or greater than or equal to 3 ppm, or greater than or equal to 5 ppm.

For example, the compound(s) of the series F-230 may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-230 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-240, each (except for F-240db and except for F-240aa, which may also lead to F-1234yf) being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-240 (except for F-240db and F-240aa) in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-240 (except for F-240db and F-240aa) may then be present in a content of greater than or equal to 1 ppm, or greater than or equal to 2 ppm, or greater than or equal to 3 ppm, or greater than or equal to 5 ppm. Similarly, the total content of compounds of the series F-240 (except for F-240db and F-240aa) in the composition may be greater than or equal to 1 ppm, or greater than or equal to 2 ppm, or greater than or equal to 3 ppm, or greater than or equal to 5 ppm.

For example, the compound(s) of the series F-240 (except for F-240db and F-240aa) may be present in a content of 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-240 (except for F-240db and F-240aa) in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

More particularly, the total content of F-240fa in the composition may be between 1 and 500 ppm, advantageously between 10 and 500 ppm, preferably between 50 and 450 ppm.

F-240db and F-240aa may be present in amounts markedly higher than those listed above. For example, the total content of F-240aa may be greater than 0.1%.

The compositions according to the invention may especially comprise one or more compounds of the series F-250, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-250 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-250 may then be present in a content of greater than or equal to 1 ppm, or greater than or equal to 2 ppm, or greater than or equal to 3 ppm, or greater than or equal to 5 ppm. Similarly, the total content of compounds of the series F-250 in the composition may be greater than or equal to 1 ppm, or greater than or equal to 2 ppm, or greater than or equal to 3 ppm, or greater than or equal to 5 ppm.

For example, the compound(s) of the series F-250 may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-250 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-260, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-260 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-260 may be present in a content of greater than or equal to 1 ppm, or greater than or equal to 2 ppm, or greater than or equal to 3 ppm, or greater than or equal to 5 ppm. Similarly, the total content of compounds of the series F-260 in the composition may be greater than or equal to 1 ppm, or greater than or equal to 2 ppm, or greater than or equal to 3 ppm, or greater than or equal to 5 ppm.

For example, the compound(s) of the series F-260 may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-260 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise F-1210xa in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that F-1210xa may then be present in a content of greater than or equal to 1 ppm, or greater than or equal to 2 ppm, or greater than or equal to 3 ppm, or greater than or equal to 5 ppm.

For example, F-1210xa may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

The compositions according to the invention may especially comprise one or more compounds of the series F-1220, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1220 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-1220 may then be present in a content of greater than or equal to 1 ppm, or greater than or equal to 2 ppm, or greater than or equal to 3 ppm, or greater than or equal to 5 ppm. Similarly, the total content of compounds of the series F-1220 in the composition may be greater than or equal to 1 ppm, or greater than or equal to 2 ppm, or greater than or equal to 3 ppm, or greater than or equal to 5 ppm.

For example, the compound(s) of the series F-1220 may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1220 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-1230, each (except for F-1230xf and F-1230xa, which are precursors of F-1234yf) being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1230 (with the exception of F-1230xf and F-1230xa) in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-1230 (except for F-1230xa and F-1230xf) may then be present in a content of greater than or equal to 1 ppm, or greater than or equal to 2 ppm, or greater than or equal to 3 ppm, or greater than or equal to 5 ppm. Similarly, the total content of compounds of the series F-1230 (except for F-1230xa and F-1230xf) in the composition may be greater than or equal to 1 ppm, or greater than or equal to 2 ppm, or greater than or equal to 3 ppm, or greater than or equal to 5 ppm.

For example, the compound(s) of the series F-1230 (except for F-1230xa and F-1230xf) may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1230 (except for F-1230xa and F-1230xf) in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

F-1230xf and F-1230xa may be present in amounts markedly higher than those listed above.

The compositions according to the invention may especially comprise one or more compounds of the series F-1240, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1240 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-1240 may then be present in a content of greater than or equal to 1 ppm, or greater than or equal to 2 ppm, or greater than or equal to 3 ppm, or greater than or equal to 5 ppm. Similarly, the total content of compounds of the series F-1240 in the composition may be greater than or equal to 1 ppm, or greater than or equal to 2 ppm, or greater than or equal to 3 ppm, or greater than or equal to 5 ppm.

For example, the compound(s) of the series F-1240 may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1240 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-1250, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1250 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that the compound(s) of the series F-1250 may then be present in a content of greater than or equal to 1 ppm, or greater than or equal to 2 ppm, or greater than or equal to 3 ppm, or greater than or equal to 5 ppm. Similarly, the total content of compounds of the series F-1250 in the composition may be greater than or equal to 1 ppm, or greater than or equal to 2 ppm, or greater than or equal to 3 ppm, or greater than or equal to 5 ppm.

For example, the compound(s) of the series F-1250 may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1250 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

F-1243zf, which has induced cardiac toxicity in rats exposed subchronically, is a particularly undesirable impurity. Although the mechanism of action of this effect and its pertinence for man is not established at the present time, the maximum accepted content of F-1243zf in F-1234yf might be very low. Now, F-1243zf forms a quasi-azeotrope with F-1234yf. These two compounds are thus inseparable by standard distillation.

Consequently, it is desirable to adjust the compositions according to the invention so as to limit the presence of precursors of F-1243zf therein.

Possible precursors of F-1243zf (by fluorination reaction) are F-1240za, F-1240zf, F-250fb (via one of the two preceding compounds), F-250da (via F-1240za) and F-250db (via F-1240zf).

Thus, advantageous compositions according to the invention:
  comprise at least one compound from among those of the series F-1240 and F-250, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
  comprise one or more compounds from among those of the series F-1240 and F-250, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
  comprise at least one compound from among F-1240za, F-1240zf, F-250fb, F-250da and F-250db, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
  comprise one or more compounds from among F-1240za, F-1240zf, F-250fb, F-250da and F-250db, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

F-1225ye also showed a certain degree of toxicity in rats exposed subchronically. Moreover, it is a flammable substance. It is thus desirable to limit its presence in mixture with F-1234yf (for example to a content of less than or equal to 5 ppm), and to do this, it is desirable to limit the presence of its precursors in mixture with F-240db.

Possible precursors of F-1225ye (by fluorination reaction) are F-1220xd, F-230da (via F-1220xd) and F-230ab (via F-1220xd).

Thus, advantageous compositions according to the invention:
  comprise at least one compound from among those of the series F-1220 and F-230, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
  comprise one or more compounds from among those of the series F-1220 and F-230, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise at least one compound from among F-1220xd, F-230da and F-230ab, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among F-1220xd, F-230da and F-230ab, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

F-1225zc is another compound that has various potential toxicological effects. It is thus desirable to limit its presence in F-1234yf. However, its boiling point is close to that of F-1234yf, which makes its separation by standard distillation difficult.

Consequently, it is desirable to adjust the compositions according to the invention so as to limit the presence of precursors of F-1225zc therein.

Possible precursors of F-1225zc (by fluorination reaction) are F-1220za, F-230fa (via F-1220za) and F-230da (via F-1220za).

Thus, advantageous compositions according to the invention:

comprise at least one compound from among F-1220za, F-230fa and F-230da, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among F-1220za, F-230fa and F-230da, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

More generally, it is thought that, due to their reactivity, the molecules that bear a group $=CF_2$ also have risks of toxicological effects. This concerns, besides F-1225zc, F-1234yc, F-1234zc, F-1225yc, F-1243zc, F-1243yc, F-1252zc and F-1216yc. Among these compounds, the most troublesome are F-1216yc, F-1243yc and F-1252zc, due to the difficulties in separating these compounds from F-1234yf due to their boiling point that is close to that of F-1234yf.

Consequently, it is desirable to adjust the compositions according to the invention so as to limit the presence of precursors of F-1216yc therein.

Possible precursors of F-1216yc (by fluorination reaction) are F-1210xa, F-220da (via F-1210xa) and F-220aa (via F-1210xa).

Thus, advantageous compositions according to the invention:

comprise at least one compound from among those of the series F-1210 and F-220, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among those of the series F-1210 and F-220, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise at least one compound from among F-1210xa, F-220da and F-220aa, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among F-1210xa, F-220da and F-220aa, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

It is also desirable to adjust the compositions according to the invention so as to limit the presence of precursors of F-1243yc therein.

Possible precursors of F-1243yc (by fluorination reaction) are F-1240xa and F-250ab (via F-1240xa).

Thus, advantageous compositions according to the invention:

comprise at least one compound from among F-1240xa and F-250ab, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among F-1240xa and F-250ab, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

It is also desirable to adjust the compositions according to the invention so as to limit the presence of precursors of F-1252zc therein.

Possible precursors of F-1252zc (by fluorination reaction) are F-1250za, F-260fb (via F-1250za) and F-260db (via F-1250za).

Thus, advantageous compositions according to the invention:

comprise at least one compound from among those of the series F-1250 and F-260, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among those of the series F-1250 and F-260, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise at least one compound from among F-1250za, F-260fb and F-260db, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among F-1250za, F-260fb and F-260db, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Moreover, F-1234ze is a substance which should not be present in excessively large amount in mixture with F-1234yf. For example, the content of F-1234ze in F-1234yf should remain less than or equal to 500 ppm. Now, the boiling point of F-1234ze is close to that of F-1234yf, which makes a separation by conventional distillation difficult. For this reason, it is desirable to limit the presence of precursors of F-1234ze in mixture with F-240db.

Possible precursors of F-1234ze (by fluorination reaction) are F-1230za, F-1230zd, F-240fa and F-240da.

Thus, advantageous compositions according to the invention:

comprise at least one compound from among F-1230za, F-1230zd, F-240fa and F-240da, in a content: less than or equal to 500 ppm; or from 400 to 500 ppm; or from 300 to 400 ppm; or from 200 to 300 ppm; or from 100 to 200 ppm; or less than or equal to 100 ppm, and for example from 1 to 100 ppm; or else comprise one or more compounds from among F-1230za, F-1230zd, F-240fa and F-240da, the total content of all these compounds being: less than or equal to 500 ppm; or from 400 to 500 ppm; or from 300 to 400 ppm; or from 200 to 300 ppm; or from 100 to 200 ppm; or less than or equal to 100 ppm, and for example from 1 to 100 ppm.

Taking into account the foregoing, advantageous compositions according to the invention:

comprise one or more compounds from among F-1240za, F-1240zf, F-250fb, F-250da and F-250db, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; and also comprise one or more compounds from among F-1220za, F-230fa and F-230da, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; and also comprise one or more compounds from among F-1210xa, F-220da and F-220aa, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; and also comprise one or more compounds from among F-1240xa and F-250ab, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; and also comprise one or more compounds from among F-1250za, F-260fb and F-260db, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; and also comprise one or more compounds from among F-1220xd, F-230da and F-230ab, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; and also comprise one or more compounds from among F-1230za, F-1230zd, F-240fa and F-240da, the total content of all these compounds being: less than or equal to 500 ppm; or from 400 to 500 ppm; or from 300 to 400 ppm; or from 200 to 300 ppm; or from 100 to 200 ppm; or less than or equal to 100 ppm, and for example from 1 to 100 ppm.

In addition, F-250fb, F-1240za and F-1240zf may be intermediate compounds in the production of F-240db, as outlined above. They are moreover precursors of F-1243zf and of F-1243yc. Consequently, advantageous compositions according to the invention:

comprise at least one compound from among F-250fb, F-1240za and F-1240zf, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else comprise one or more compounds from among F-250fb, F-1240za and F-1240zf, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Preparation of the Compositions According to the Invention

The manufacture of F-240db is known, for example, from U.S. Pat. No. 8,304,589, to which reference is expressly made herein. The document proposes a three-step process:

reaction of carbon tetrachloride with ethylene to produce F-250fb;

thermal dehydrochlorination of F-250fb to obtain F-1240za or F-1240zf; and addition of chlorine to F-1240za or F-1240zf to obtain F-240db.

Certain variants of this process are also described in U.S. Pat. No. 4,650,914, US 2009/0 216 055, US 2014/0 206 911 and US 2013/0 165 705, to which reference is expressly made herein.

A two-step process may also be envisaged, as described in U.S. Pat. No. 3,446,859, to which reference is expressly made herein:

reaction of methyl chloride with tetrachloroethylene to produce F-1230xa;

hydrochlorination of F-1230xa to obtain F-240db.

A one-step process may also be envisaged by reaction of dichloromethane with trichloroethylene.

The compositions according to the invention may then be obtained by performing one or more steps of separation of F-240db with respect to the other compounds mentioned above.

These separation steps may preferably be performed by absorption/washing and distillation. As an alternative to standard distillation or in combination therewith, it is also possible to envisage a separation by extractive distillation, physicochemical separations on molecular sieves, alumina or active charcoal or a membrane separation.

A first separation is generally performed using a distillation (column with plates, column with packing) at atmospheric pressure or under reduced pressure. The pressure chosen is less than 760 mmHg, preferentially less than 450 mmHg and more preferentially less than 200 mmHg. Inherently, the pressure of the column determines the temperature conditions for a given degree of separation. F-240db may be recovered by performing the distillation at a temperature below 180° C., preferentially below 160° C. and more preferentially below 130° C. A simple column or a distillation train may be used. Under chosen conditions, the purity of F-240db after distillation reaches a minimum of 99.8%.

A second separation may be performed using adsorption on zeolite or active charcoal.

The zeolites or active charcoals that may be used in the process for purifying F-240db advantageously have a mean pore size of from 3.4 to 11 Å, preferably from 3.4 to 10 Å. If the zeolite or the active charcoal has a mean pore size of greater than 11 Å, the amount of F-240db adsorbed increases, whereas if the mean pore size is less than 3.4 Å, the adsorption capacity of the zeolite or of the active charcoal is reduced.

Zeolite preferably has an Si/Al ratio of two or less. If the Si/Al ratio of the zeolite is greater than two, certain impurities are liable to be not selectively adsorbed. The zeolite is preferably at least one element chosen from the group consisting of 4 A molecular sieves, a 5 A molecular sieve, a 10× molecular sieve and 13× molecular sieves. Using these zeolites, the water content in F-240db may also be simultaneously reduced.

The zeolite and the active charcoal are preferably used individually for the purpose of regenerating the adsorbent, but they may also be used as a mixture. The proportions of zeolite and of active charcoal in the mixture are not particularly important, but it is preferable to use a larger amount of zeolite, which makes it possible to reduce the water content in F-240db.

To treat F-240db with zeolite and/or active charcoal in the liquid phase, a batch process or a continuous process may be used. Industrially, a process that consists in continuously passing F-240db over a fixed bed is preferable. The liquid space time velocity (LSTV) may be chosen appropriately as a function of the content of impurities to be removed and of the amount of F-240db to be treated. In general, the space velocity is preferably from 1 to 50 h$^{-1}$. Industrially, the purification process may alternately use two adsorption towers.

The treatment temperature of F-240db is from 0° C. to 120° C., preferably from 20° C. to 80° C. If the treatment temperature is greater than 120° C., the cost of equipment may increase on account of the heating of the apparatus, whereas if the treatment temperature is below 0° C., cooling equipment may be necessary. The pressure is from 0 to 3 MPa, preferably from 0 to 1 MPa. If the pressure is greater than 3 MPa, the economic viability may reduce on account of the requirements in terms of pressure resistance of the apparatus.

A membrane separation technique may also be performed in addition to adsorption on active charcoal or on zeolite, or as an alternative to these techniques. Membrane separation may be performed in the gas phase according to a continuous process performed at low pressure, or at reduced pressure. The chosen pressure is less than 5 bar, preferentially less than 2 bar and more preferentially below atmospheric pressure. The choice of the membrane depends on the properties of the impurities to be separated from the F-240db (difference in solubility, in diffusivity and in permeability). Membrane separation is performed at a temperature that depends on the chosen pressure, below 250° C., preferentially below 230° C. and more preferentially below 180° C.

When F-240db containing impurities is placed in contact with zeolite and/or active charcoal in the liquid phase and/or is purified on a membrane in the gas phase under the conditions described above, F-240db may be obtained with a purity of greater than 99.9%.

Manufacture of F-1234yf

The compositions according to the invention may be used for manufacturing F-1234yf having desired specifications, via one or more fluorination steps.

The fluorination is preferably a catalytic fluorination in the gas phase with HF.

The catalyst used may be, for example, based on a metal comprising a transition metal oxide or a derivative or a halide or an oxyhalide of such a metal. Examples that may be mentioned include $FeCl_3$, chromium oxyfluoride, chromium oxides (optionally subjected to fluorination treatments), chromium fluorides, and mixtures thereof. Other possible catalysts are catalysts supported on charcoal, antimony-based catalysts, aluminum-based catalysts (for example $AlF_3$ and $Al_2O_3$, alumina oxyfluoride and alumina fluoride).

A chromium oxyfluoride, an aluminum fluoride or oxyfluoride, or a supported or unsupported catalyst containing a metal such as Cr, Ni, Fe, Zn, Ti, V, Zr, Mo, Ge, Sn, Pb, Mg, Sb may generally be used.

Reference may be made in this respect to WO 2007/079 431 (on page 7, lines 1-5 and 28-32), to EP 939 071 (paragraph [0022]), to WO 2008/054 781 (on page 9, line 22—page 10, line 34) and to WO 2008/040 969 (claim 1), to which reference is expressly made.

The catalyst is particularly preferably based on chromium and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5 to 20% by weight of chromium and from 0.5% to 20% by weight of nickel, preferably from 2% to 10% of each.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support that has or has not been subjected to an activation.

Reference may be made to WO 2009/118 628 (especially on page 4, line 30—page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

For example, the catalyst is preferably subjected to activation with air or oxygen and HF at a temperature of from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, of HF and of organic compounds.

The HF/organic compounds mole ratio is preferably from 2 to 40 and the oxidizing agent/organic compounds mole ratio is preferably from 0.04 to 25. The final activation temperature is preferably from 300 to 400° C. and its duration is preferably from 6 to 100 hours.

The gas-phase fluorination reaction may be performed:
with an HF/chlorinated compound mole ratio of from 1:1 to 150:1, preferably from 3:1 to 100:1 and particularly preferably from 5:1 to 50:1;
with a contact time of from 1 to 100 s, preferably 1 to 50 s and more particularly 2 to 40 s (volume of catalyst divided by the total entering stream, adjusted to the operating temperature and pressure);
at an absolute pressure ranging from 0.1 to 50 bar, preferably from 0.3 to 15 bar;
at a temperature (temperature of the catalytic bed) of from 100 to 500° C., preferably from 200 to 450° C. and more particularly from 250 to 400° C.

The duration of the reaction step is typically from 10 to 2000 hours, preferably from 50 to 500 hours and more particularly preferably from 70 to 300 hours.

An oxidizing agent, preferably oxygen, may optionally be added during the fluorination reaction. The oxygen/organic compounds mole ratio may be from 0.005 to 2, preferably from 0.01 to 1.5. The oxygen may be introduced in pure form or in the form of air or an oxygen/nitrogen mixture. The oxygen may also be replaced with chlorine.

The stream of products obtained from the fluorination may undergo suitable treatments (distillation, washing, etc.) so as to recover F-1234yf in purified form and to separate out other compounds present (HCl, unreacted HF, unreacted F-240db, and other organic compounds). One or more streams may undergo recycling.

Catalyst regeneration steps may also be envisaged, as described, for example, in WO 2012/098 421 and WO 2012/098 422, to which reference is expressly made.

A production of F-1234yf in two steps may also be envisaged: first fluorination of the composition based on F-240db to produce F-1233xf, followed by fluorination of the latter to produce F-1234yf. The same reactor or successive reactors may be used to perform these steps. This type of process is especially described in WO 2013/088 195, to which reference is expressly made.

The stream of F-1234yf obtained, preferably, contains:
less than 500 ppm, or 250 ppm, or 200 ppm, or 150 ppm, or 100 ppm, or 50 ppm, or 25 ppm, or 10 ppm, or 5 ppm, of F-1243zf; and/or
less than 500 ppm, or 250 ppm, or 200 ppm, or 150 ppm, or 100 ppm, or 50 ppm, or 25 ppm, or 10 ppm, or 5 ppm, of F-1225zc; and/or
less than 500 ppm, or 250 ppm, or 200 ppm, or 150 ppm, or 100 ppm, or 50 ppm, or 25 ppm, or 10 ppm, or 5 ppm, of F-1216yc; and/or
less than 500 ppm, or 250 ppm, or 200 ppm, or 150 ppm, or 100 ppm, or 50 ppm, or 25 ppm, or 10 ppm, or 5 ppm, of F-1243yc; and/or
less than 500 ppm, or 250 ppm, or 200 ppm, or 150 ppm, or 100 ppm, or 50 ppm, or 25 ppm, or 10 ppm, or 5 ppm, of F-1252zc; and/or
less than 500 ppm, or 250 ppm, or 200 ppm, or 150 ppm, or 100 ppm, or 50 ppm, or 25 ppm, or 10 ppm, or 5 ppm, of F-1225ye; and/or
less than 500 ppm, or 250 ppm, or 200 ppm, or 150 ppm, or 100 ppm, or 50 ppm, or 25 ppm, or 10 ppm, or 5 ppm, of F-1234ze.

Preferably, these contents are obtained on conclusion of the fluorination, without (or before any) step of purification of the product stream.

EXAMPLES

The examples below illustrate comparatively the fluorination reaction of compositions based on F-240db to obtain F-1234yf.

The catalyst used (50 mL) is a bulk catalyst based on chromium oxide.

The activation comprises the following steps:
a step of drying at atmospheric pressure under a stream of nitrogen at a temperature of about 275° C. for 120 hours;
a first step of activation at a temperature of about 275° C. under a mixture of nitrogen and hydrofluoric acid, gradually reducing the nitrogen over 41 hours. A stage under pure HF is then observed for 41 hours, while increasing the temperature to 350° C.;
a second step of activation with air for 101 hours at 350° C. before performing the fluorination reaction.

Example 1

In this example, a fluorination reaction is performed using a composition containing F-240db with a high purity (content of F-240db greater than 99.95%).

The reaction conditions are as follows:
HF/F240db mole ratio: 20;
oxygen/F-240db mole ratio: 0.2;
contact time: 10 s;
pressure: atmospheric pressure;
temperature: 350° C.

After 125 hours under these conditions, the gas stream exiting the reactor is analyzed, after washing, by gas chromatography. The conversion of the F-240db is 100%. Analysis of the stream is reported in the table below (values in mol %):

| Product detected | Concentration |
| --- | --- |
| CO | 0.91 |
| $CO_2$ | 1.50 |
| F-143a | 0.23 |
| F-1234yf | 8.31 |
| F-245cb | 1.84 |
| F-1233xf | 85.98 |
| F-1223xd | 1.23 |
| Others | traces |

On conclusion of this preliminary reaction step, the products are separated by distillation on a packing column of Sulzer type. The F-1234yf obtained is very pure (purity greater than 99.95%).

Example 2

In this example, the fluorination reaction is performed using a composition containing 99.43% of F-240db and 0.57% of F-250fb.

The reaction conditions are as follows:
HF/chlorinated organics mole ratio: 20;
oxygen/chlorinated organics mole ratio: 0.2;
contact time: 10 s;
pressure: atmospheric pressure;
temperature: 350° C.

After 51 hours under these conditions, the gas stream exiting the reactor is analyzed, after washing, by gas chromatography. The conversion of the F-240db and of the F-250fb is 100%. Analysis of the stream is reported in the table below (values in mol %):

| Product detected | Concentration |
| --- | --- |
| CO | 1.63 |
| $CO_2$ | 0.82 |
| F-143a | 0.22 |
| F-1243zf | 0.54 |
| F-1234yf | 12.67 |
| F-245cb | 3.02 |
| F-1242zf | traces |
| F-1233xf | 80.49 |
| F-253fb | traces |
| F-1223xd | 0.61 |
| Others | traces |

On conclusion of this preliminary reaction step, the products are separated by distillation on a packing column of Sulzer type. The results obtained show that F-1243zf and F-1234yf are not separated by distillation.

Industrially, the use of such a starting material would lead to the production of a stream of F-1234yf containing more than 500 ppm of F-1243zf.

Example 3

In this example, a fluorination reaction is performed on a composition containing 99.62% of F-240db and 0.38% of F-230fa.

The reaction conditions are the same as in Example 2.

After 62 hours under these conditions, the gas stream exiting the reactor is analyzed, after washing, by gas chromatography. The conversion of the F-240db and of the F-230fa is 100%. Analysis of the stream is reported in the table below (values in mol %):

| Product detected | Concentration |
| --- | --- |
| CO | 2.03 |
| $CO_2$ | 1.32 |
| F-143a | 0.19 |
| F-1225zc | 0.02 |
| F-1234yf | 11.04 |
| F-245cb | 2.41 |
| F-236fa | 0.18 |
| F-1224 | 0.04 |
| F-1233xf | 81.51 |
| F-226da | traces |
| F-235fa | 0.01 |
| F-1214 | traces |
| F-1223xd | 1.24 |
| F-1213xa | 0.01 |
| Unknown | traces |

On conclusion of this preliminary reaction step, the products are separated by distillation on a packing column of Sulzer type. The results obtained show that F-1225zc and F-1234yf are poorly separated by distillation.

Industrially, the use of such a starting material would lead to the production of a stream of F-1234yf containing more than 500 ppm of F-1225zc.

The invention claimed is:

1. A composition comprising at least 99% by weight of 1,1,1,2,3-pentachloropropane and at least one additional compound selected from the group consisting of trichloropropanes, tetrachloropropanes other than F-250fb, pentachloropropanes other than 1,1,1,2,3-pentachloropropane, hexachloropropanes, heptachloropropanes, dichloropropenes, trichloropropenes other than F-1240za, tetrachloropropenes, pentachloropropenes and hexachloropropene, said additional compound being present in the composition in a weight content of less than or equal to 500 ppm.

2. The composition as claimed in claim 1, wherein the additional compound is present in the composition in a weight content of less than or equal to 250 ppm.

3. The composition as claimed in claim 1, wherein the at least one additional compound comprises a plurality of additional compounds selected from the group consisting of trichloropropanes, tetrachloropropanes other than F-250fb, pentachloropropanes other than 1,1,1,2,3-pentachloropropane, hexachloropropanes, heptachloropropanes, dichloropropenes, trichloropropenes other than F-1240za, tetrachloropropenes, pentachloropropenes and hexachloropropene, each of the additional compounds of said plurality of additional compounds being present in the composition in a weight content of less than or equal to 500 ppm.

4. The composition as claimed in claim 1, wherein the at least one additional compound comprises a plurality of additional compounds selected from the group consisting of trichloropropenes, tetrachloropropanes other than F-250fb, pentachloropropanes other than 1,1,1,2,3-pentachloropropane, hexachloropropanes, heptachloropropanes, dichloropropenes, trichloropropenes other than F-1240za, tetrachloropropenes, pentachloropropenes and hexachloropropene, the total weight content of all of the additional compounds being less than or equal to 1000 ppm.

5. The composition as claimed in claim 1, which comprises at least 99.5% by weight, of 1,1,1,2,3-pentachloropropane.

6. The composition as claimed in claim 1, comprising at least 3,3,3-trichloropropene; wherein the weight content of said compound in the composition is less than or equal to 100 ppm.

7. The composition as claimed in claim 1, comprising at least one compound selected from trichloropropenes other than F-1240za and tetrachloropropanes other than F-250fb, the weight content of each of these compounds in the composition being less than or equal to 250 ppm.

8. The composition as claimed in claim 1, comprising at least one compound selected from pentachloropropenes and hexachloropropanes, the weight content of each of said compounds in the composition being less than or equal to 50 ppm.

9. The composition as claimed in claim 1, comprising at least one compound selected from hexachloropropene and heptachloropropanes, the weight content of each of said compounds in the composition being less than or equal to 50 ppm.

10. The composition as claimed in claim 1, comprising at least one compound selected from dichloropropenes and trichloropropanes, the weight content of each of these compounds in the composition being less than or equal to 50 ppm.

11. The composition as claimed in claim 1, comprising at least one compound selected from the group consisting of 1,1,3,3-tetrachloropropene, 1,3,3,3-tetrachloropropene, 1,1,1,3,3-pentachloropropane and 1,1,2,3,3-pentachloropropane, and the weight content of each of these compounds in the composition is less than or equal to 500 ppm.

* * * * *